(12) United States Patent
Walker

(10) Patent No.: US 10,518,022 B1
(45) Date of Patent: Dec. 31, 2019

(54) ENEMA APPLICATOR DEVICE

(71) Applicant: Kenroy Walker, Sunrise, FL (US)

(72) Inventor: Kenroy Walker, Sunrise, FL (US)

( * ) Notice: Subject to any disclaimer, the term of this patent is extended or adjusted under 35 U.S.C. 154(b) by 426 days.

(21) Appl. No.: 14/805,813

(22) Filed: Jul. 22, 2015

(51) Int. Cl.
A61M 3/02 (2006.01)

(52) U.S. Cl.
CPC ........ *A61M 3/0262* (2013.01); *A61M 3/0266* (2013.01); *A61M 3/0279* (2013.01)

(58) Field of Classification Search
CPC ............... A61M 31/00; A61M 3/0262; A61M 2210/1067; A61M 3/0279; A61M 2202/0482; A61M 2205/075; A61M 35/00; A61M 3/00; A61M 3/0266
See application file for complete search history.

(56) References Cited

U.S. PATENT DOCUMENTS

| 2,690,181 | A | * | 9/1954 | Boyer | A61M 3/0262 222/215 |
|---|---|---|---|---|---|
| 5,380,275 | A | | 1/1995 | Kensey et al. | |
| 5,667,146 | A | | 9/1997 | Pimentel et al. | |
| 6,632,195 | B1 | | 10/2003 | Smith | |
| 2010/0249730 | A1 | * | 9/2010 | Beechie | A61M 3/0262 604/275 |

* cited by examiner

*Primary Examiner* — Brandy S Lee

(57) ABSTRACT

An enema applicator device including a manual pump having a removable bulb portion and an L-shaped tube, a frustoconical connector having a top side, a bottom side, and an opening, an applicator portion having a frustoconical base and an applicator tube, an aperture medially and continuously disposed through the base of the applicator portion, a rubberized bulb cover continuously disposed around an exterior surface of the bulb portion of the pump, a tube cover continuously disposed around an exterior surface of the tube of the pump from a left side of the tube of the pump to proximal a right side of the tube of the pump, and a rubberized connector cover continuously disposed around an exterior surface of the connector from the top side of the connector to the tube cover.

5 Claims, 4 Drawing Sheets

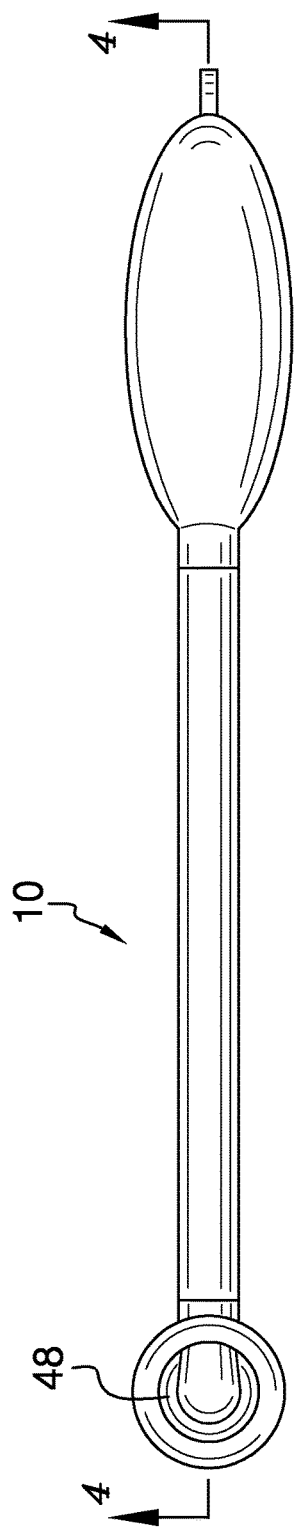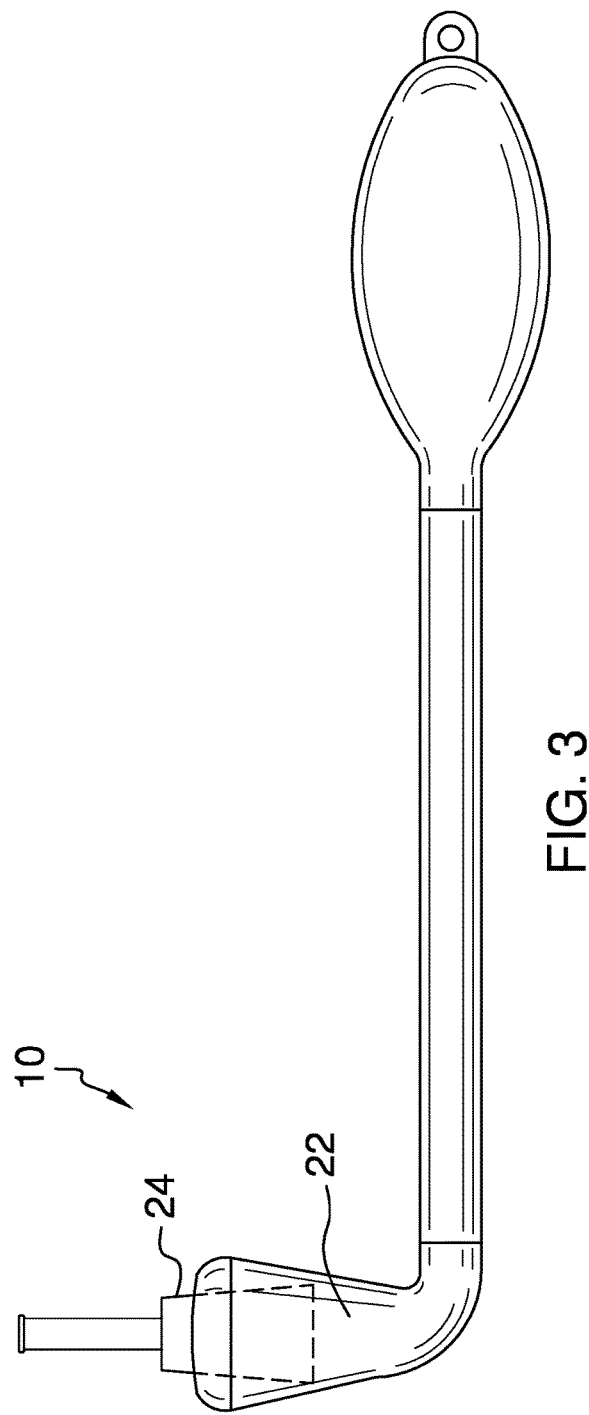

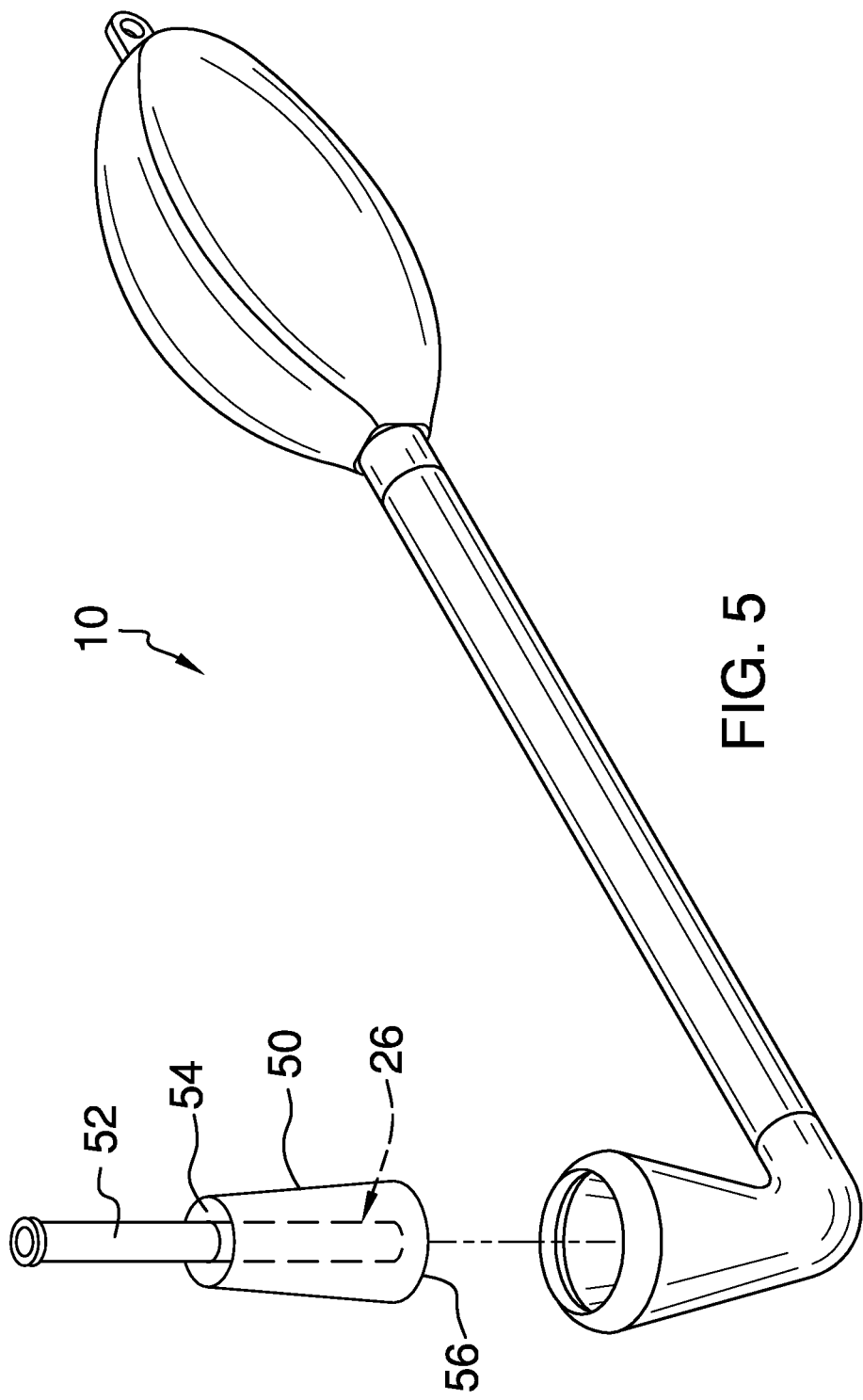

ENEMA APPLICATOR DEVICE

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

TO ALL WHOM IT MAY CONCERN

Be it known that I, Kenroy Walker, a citizen of the United States, have invented new and useful improvements in an enema applicator device as described in this specification.

BACKGROUND OF THE INVENTION

Various types of enema applicators are known in the prior art. However, what has been needed is an enema applicator device including a manual pump having a removable bulb portion and an L-shaped tube, a frustoconical connector having a top side, a bottom side, and an opening, an applicator portion having a frustoconical base removably disposed within the opening of the connector and an applicator tube medially attached to a top surface of the base of the applicator portion, an aperture medially and continuously disposed through the applicator portion, a rubberized bulb cover continuously disposed around an exterior surface of the bulb portion of the pump, a tube cover continuously disposed around an exterior surface of the tube of the pump, and a rubberized connector cover continuously disposed around an exterior surface of the connector. What has been further needed is for the applicator tube of the applicator portion to be removably insertable into a rectal opening of a user. Lastly, what has been needed is for the bulb portion of the pump to be filled with a cleansing solution to allow a user to manually pump the cleansing solution through the tube of the pump, the connector, and the applicator portion, into a rectum of the user.

Although the enema applicator device can be used by any individual to more easily insert a cleansing solution into his rectum, the device is specifically designed to be used by a disabled or physically handicapped individual. The tube on the pump enables a user to more easily insert an enema applicator into his own rectal opening, thus providing him with a greater degree of freedom and independence from his caregiver.

FIELD OF THE INVENTION

The present invention relates to enema applicators, and more particularly, to an enema applicator device.

SUMMARY OF THE INVENTION

The general purpose of the present enema applicator device, described subsequently in greater detail, is to provide an enema applicator which has many novel features that result in an enema applicator device which is not anticipated, rendered obvious, suggested, or even implied by prior art, either alone or in combination thereof.

To accomplish this, the present enema applicator device includes a manual pump, a frustoconical connector, an applicator portion, an aperture, a rubberized bulb cover, a tube cover, and a rubberized connector cover. The manual pump has a removable bulb portion and an L-shaped tube. The tube of the pump has a right side perpendicularly disposed with a left side. Each of the bulb portion of the pump and the tube of the pump has an exterior surface. The connector has a top side, a bottom side, and an opening continuously disposed through the connector from the top side of the connector to the bottom side of the connector. The bottom side of the connector is attached to the right side of the tube of the pump. A circumference of the bottom side of the connector substantially conforms to a circumference of the right side of the tube of the pump.

The applicator portion has a frustoconical base and an applicator tube. The base of the applicator portion is removably disposed within the opening of the connector proximal the top side of the connector. The applicator tube of the applicator portion is medially attached to a top surface of the base of the applicator portion. The aperture is medially and continuously disposed through the base of the applicator portion from the top surface of the base of the applicator portion to a bottom surface of the base of the applicator portion. A circumference of the applicator tube substantially conforms to a circumference of the aperture.

The bulb cover is continuously disposed around the exterior surface of the bulb portion of the pump. The tube cover is continuously disposed around the exterior surface of the tube of the pump from the left side of the tube of the pump to proximal the right side of the tube of the pump. The connector cover is continuously disposed around the exterior surface of the connector from the top side of the connector to the tube cover. The applicator tube of the applicator portion is configured to be inserted into a rectal opening of a user. The bulb portion of the pump is configured to be filled with a cleansing solution to allow a user to manually pump the cleansing solution through the pump tube, the connector, and the applicator portion and into a rectum of a user.

The enema applicator device optionally further comprises a connector cap and a removably disposable wall-mounted rack. The connector cap is removably and continuously disposed over the top side of the connector. The connector cap is configured to allow the user to cover the top side of the connector when the device is not in use. The rack has a horizontally disposed tray portion. The device is removably disposed atop the tray portion of the rack.

Thus has been broadly outlined the more important features of the present enema applicator device so that the detailed description thereof that follows may be better understood and in order that the present contribution to the art may be better appreciated.

BRIEF DESCRIPTION OF THE DRAWINGS

Figures

FIG. 2 is a top plan view.

FIG. 3 is a front elevation view.

FIG. 5 is an in-use view.

DETAILED DESCRIPTION OF THE DRAWINGS

Figure 1:
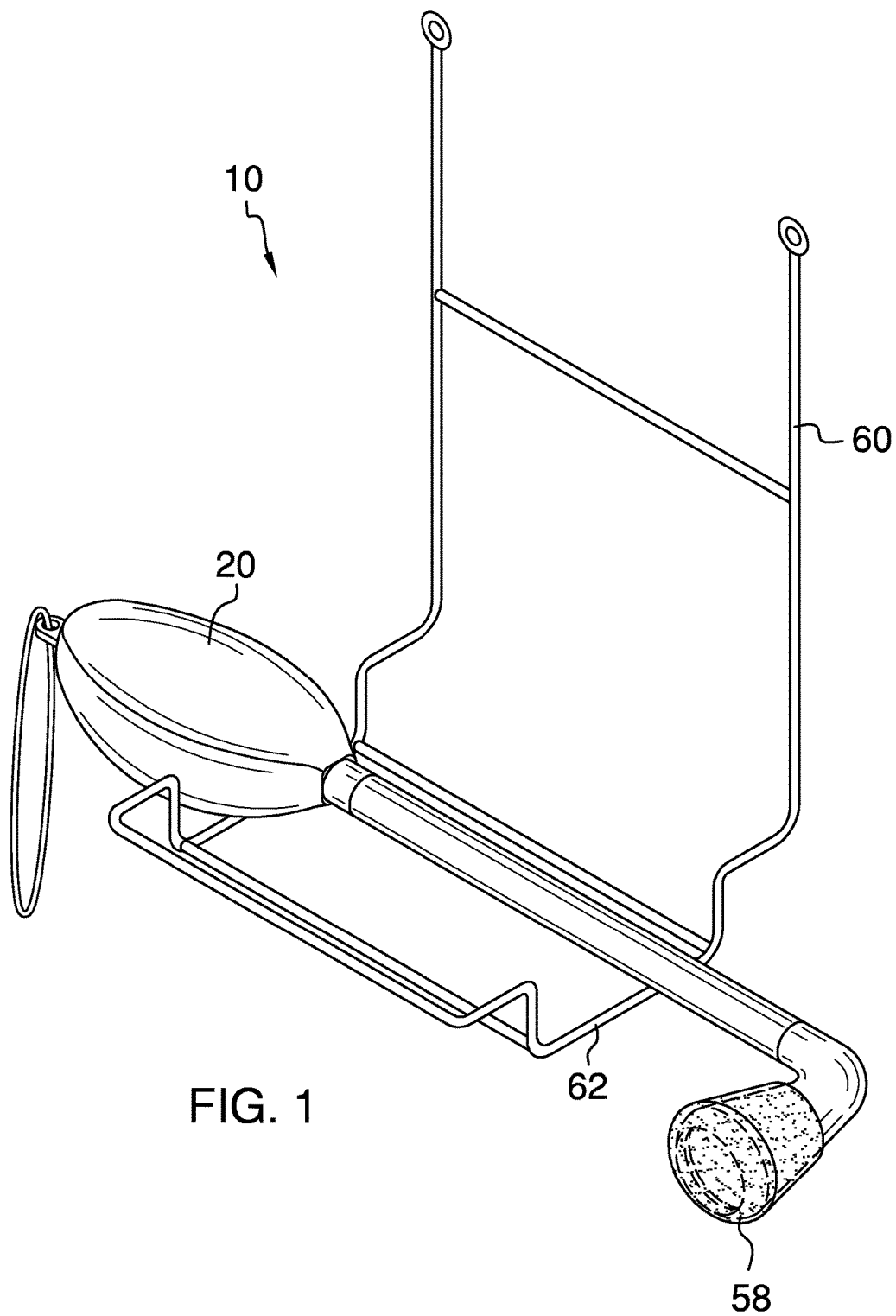
FIG. 1 is a front isometric view.
Figure 4:
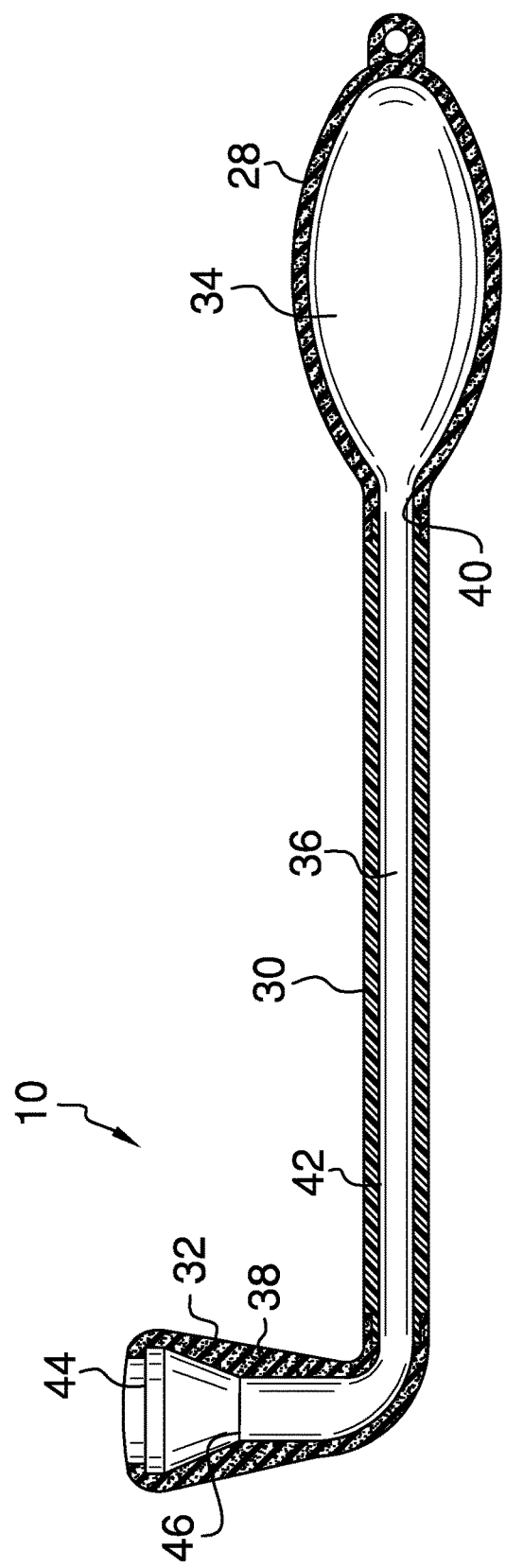
FIG. 4 is a cross-sectional view taken along line 4-4 of FIG. 2.

With reference now to the drawings, and in particular FIGS. 1 through 5 thereof, an example of the instant enema applicator device employing the principles and concepts of the present enema applicator device and generally designated by the reference number 10 will be described.

Referring to FIGS. 1 through 5, the present enema applicator device 10 is illustrated. The enema applicator device 10 includes a manual pump 20, a frustoconical connector 22, an applicator portion 24, an aperture 26, a rubberized bulb cover 28, a tube cover 30, and a rubberized connector cover 32. The pump 20 has a removable bulb portion 34 and an L-shaped tube 36. The tube 36 of the pump 20 has a right side perpendicularly disposed with a left side 40. Each of the bulb portion 34 of the pump 20 and the tube 36 of the pump 20 has an exterior surface 42. The connector 22 has a top side 44, a bottom side 46, and an opening 48 continuously disposed through the connector 22 from the top side 44 of the connector 22 to the bottom side 46 of the connector 22. The bottom side 46 of the connector 22 is attached to the right side 38 of the tube 36 of the pump 20.

The applicator portion 24 has a frustoconical base 50 and an applicator tube 52. The base 50 of the applicator portion 24 is removably disposed within the opening 48 of the connector 22 proximal the top side 44 of the connector 22. The applicator tube 52 of the applicator portion 24 is medially attached to a top surface 54 of the base 50 of the applicator portion 24. The aperture 26 is medially and continuously disposed through the base 50 of the applicator portion 24 from the top surface 54 of the base 50 of the applicator portion 24 to a bottom surface 56 of the base 50 of the applicator portion 24.

The bulb cover 28 is continuously disposed around the exterior surface 42 of the bulb portion 34 of the pump 20. The tube cover 30 is continuously disposed around the exterior surface 42 of the tube 36 of the pump 20 from the left side 40 of the tube 36 of the pump 20 to proximal the right side 38 of the tube 36 of the pump 20. The connector cover 32 is continuously disposed around the exterior surface 42 of the connector 22 from the top side 44 of the connector 22 to the tube cover 30.

The enema applicator device 10 optionally further comprises a connector cap 58 and a removably disposable wall-mounted rack 60. The connector cap 58 is removably and continuously disposed over the top side 44 of the connector 22. The rack 60 has a horizontally disposed tray portion 62. The device 10 is removably disposed atop the tray portion 62 of the rack 60.

What is claimed is:

1. An enema applicator device comprising:
a manual pump having a removable bulb portion and an L-shaped tube the L-shaped tube, having a distal side relative to the bulb portion perpendicularly disposed with a proximal side relative to the bulb portion, each of the bulb portion and the tube having an exterior surface;
a frustoconical connector having a larger side, a smaller side, and an opening continuously disposed through the connector from the larger side to the smaller side, wherein the smaller side is attached to the distal side of the tube of the pump;
wherein a circumference of the smaller side substantially conforms to a circumference of the distal side of the tube of the pump;
an applicator portion having a frustoconical base removably disposed within the connector opening proximal the larger side and an applicator tube medially attached to and extending from a first surface of the applicator portion base;
an aperture medially and continuously disposed through the applicator portion base from the first surface of the applicator portion base to a second surface of the applicator portion base;
wherein a circumference of the applicator tube substantially conforms to a circumference of the aperture;
a rubberized bulb cover continuously disposed around the exterior surface of the pump bulb portion;
a tube cover continuously disposed around the exterior surface of the pump tube from the proximal side of the pump tube to proximal the distal side of the pump tube; and
a rubberized connector cover continuously disposed around the exterior surface of the connector from the connector larger side to the tube cover;
wherein the applicator tube of the applicator portion is configured to be inserted into a rectal opening of a user;
wherein the pump bulb portion is configured to be filled with a cleansing solution to allow a user to manually pump the cleansing solution through the pump tube, the connector, and the applicator portion, and into a rectum of a user.

2. The enema applicator device of claim 1 further comprising a connector cap removably and continuously disposed over the connector larger side, wherein the connector cap is configured to allow the user to cover the connector larger side when the device is not in use.

3. The enema applicator device of claim 1 further comprising a removably disposable wall-mounted rack having a horizontally disposed tray portion, wherein the device is removably disposed atop the tray portion of the rack.

4. The enema applicator device of claim 1 wherein the tube cover is plastic.

5. An enema applicator device comprising:
a manual pump having a removable bulb portion and an L-shaped tube the L-shaped tube having a distal side relative to the bulb portion perpendicularly disposed with a proximal side relative to the bulb portion, each of the bulb portion and the tube having an exterior surface;
a frustoconical connector having a larger side, a smaller side, and an opening continuously disposed through the connector from the larger side to the smaller side, wherein the smaller side is attached to the distal side of the tube of the pump;
wherein a circumference of the smaller side substantially conforms to a circumference of the distal side of the tube of the pump;
an applicator portion having a frustoconical base removably disposed within the connector opening proximal the larger side and an applicator tube medially attached to and extending from a first surface of the applicator portion base;
an aperture medially and continuously disposed through the applicator portion base from the first surface of the applicator portion base to a second surface of the applicator portion base;
wherein a circumference of the applicator tube substantially conforms to a circumference of the aperture;

a rubberized bulb cover continuously disposed around the exterior surface of the pump bulb portion;

a tube cover continuously disposed around the exterior surface of the pump tube from the proximal side of the pump tube to proximal the distal side of the pump tube; and a rubberized connector cover continuously disposed around the exterior surface of the connector from the connector larger side to the tube cover;

wherein the applicator tube of the applicator portion is configured to be inserted into a rectal opening of a user;

wherein the pump bulb portion is configured to be filled with a cleansing solution to allow a user to manually pump the cleansing solution through the pump tube, the connector, and the applicator portion, and into a rectum of a user;

a connector cap removably and continuously disposed over the connector top side;

wherein the connector cap is configured to allow a user to cover the connector larger side when the device is not in use; and a removably disposable wall-mounted rack having a horizontally disposed tray portion;

wherein the device is removably disposed atop the tray portion of the rack.

\* \* \* \* \*